(12) United States Patent
Sykes et al.

(10) Patent No.: US 6,672,761 B2
(45) Date of Patent: Jan. 6, 2004

(54) X-RAY SYSTEM

(75) Inventors: Robert John Sykes, Tendring (GB); William Thomas Luke Walker, Sudbury (GB); Benjamin Kingsley Stuart Pcecock, Long Melford (GB); David Terence Lilley, Clacton-on-Sea (GB); Andrew Glyn Richard Cartwright, Clacton-on-Sea (GB); Steven Jeffrey Humc Ainsworth, Clacton-on-Sea (GB)

(73) Assignee: Dage Precision Industries, Inc., Buckinghamshire (GB)

( * ) Notice: Subject to any disclaimer, the term of this patent is extended or adjusted under 35 U.S.C. 154(b) by 0 days.

(21) Appl. No.: 09/957,924

(22) Filed: Sep. 21, 2001

(65) Prior Publication Data

US 2002/0090057 A1 Jul. 11, 2002

(30) Foreign Application Priority Data

Sep. 21, 2000 (GB) ............................................. 0023194
Mar. 13, 2001 (GB) ............................................. 0106153

(51) Int. Cl.[7] ................................................. H05G 1/00
(52) U.S. Cl. ......................................... 378/208; 378/19
(58) Field of Search ................................ 378/208, 203, 378/198, 4, 19; 382/128

(56) References Cited

U.S. PATENT DOCUMENTS

| 5,394,455 | A | * | 2/1995 | Roeck et al. | 378/98.3 |
| 5,623,560 | A | * | 4/1997 | Nakajima et al. | 382/295 |
| 6,385,283 | B1 | * | 5/2002 | Stein et al. | 378/54 |
| 6,396,897 | B1 | * | 5/2002 | Ebrahimifard et al. | 378/4 |
| 6,421,412 | B1 | * | 7/2002 | Hsieh et al. | 378/9 |
| 6,501,818 | B1 | * | 12/2002 | Ali et al. | 378/4 |

* cited by examiner

Primary Examiner—Edward J. Glick
Assistant Examiner—Irakli Kiknadze
(74) Attorney, Agent, or Firm—Kilpatrick Stockton LLP

(57) ABSTRACT

A method of controlling an X-ray system and a cabinet for an X-ray system. The method comprises viewing a first virtual X-ray image of an object, manipulating the first image to best show an area of interest, and generating a second image in real time corresponding to the area of interest. The cabinet comprises an inner housing having an open mouth and being fully insertable with a clearance in an outer housing having an open mouth, the inner and outer housings being attachable to secure and space the housings in a predetermined relationship. Lead shielding comprises a substantially complete intermediate layer extending between the inner and outer housings and the open mouth is provided with a lead lined closure.

5 Claims, 4 Drawing Sheets

X-RAY SYSTEM

This invention relates to an x-ray system, particularly a system for viewing the internal structure of miniature electrical devices.

Miniature electrical devices are known with external electrical bonds whereby an electrical lead is soldered to the device. These kind of bonds are visually inspected, usually with a magnification device because they are too small to be seen by the naked eye. Typically such bonds may be a few microns in diameter.

More recently such devices have included electrical bonds formed at a planar interface of two electrical components. Such bonds are of course hidden from the naked eye by the face to face contact, and it has been proposed to inspect such bonds using an x-ray inspection device.

The aim of the present invention is to provide an x-ray inspection device which has improvements in design, manufacture and use.

A first aspect of the invention relates to a cabinet for an x-ray inspection system. In general terms the cabinet comprises a frame to provide mechanical support for the system components, and an enclosure to provide protection against mechanical, electrical and radiation hazards.

A known cabinet comprises a skeletal frame to which are attached infill panels, and which is designed to support the x-ray system and associated mechanical and electrical equipment. Lead sheet is applied to the frame to contain radiation, followed by external cladding panels.

A significant problem with this kind of construction is that it is very time consuming and expensive to manufacture and assemble the elements of the frame, and the infill and cladding panels to be attached to the frame. It is also problematic to ensure that the lead shielding fits closely to the frame, and is thus fully effective. An additional problem is that it is very difficult to shield that portion of the frame which protrudes to the exterior to provide an attachment for the external cladding panels. Furthermore, a skeletal frame has spaced frame members which may not be adaptable to a different internal configuration of components, without the use of adapter plates, sub-frames or the like.

According to a first aspect of the present invention, a cabinet for an x-ray system comprises an inner housing having an open mouth and being fully insertable with a clearance in an outer housing having an open mouth, the inner and outer housings having attachment means to secure and space the housings in a predetermined relationship, wherein lead shielding comprises a substantially complete intermediate layer extending between the inner and outer housings, and wherein the open mouth is provided with a lead lined closure.

Such a construction provides a relatively light and inherently stiff cabinet by virtue of the spacing of the inner and outer housings. The intermediate lead shielding is preferably applied to substantially the whole exterior of the inner housing before assembly of the outer housing, and is relatively easy to apply because the prior art frame is absent. Special shielding measures need to be taken in the region of attachments of the inner and outer housings, but these are less of a problem than with the prior cabinet construction, in which the skeletal frame protrudes to the exterior; these attachments may in any event be formed after application of the lead shielding in the inner housing. The cabinet according to this aspect of the invention is significantly less expensive to manufacture and assemble than the prior cabinet.

The cabinet of the invention has the particular virtue that the outer housing, which replaces the prior art external cladding, contributes to the strength and rigidity of the cabinet whilst completely enclosing the lead shielding. Furthermore the outer housing comprises an unitary shell for the lead shielding, and can maintain the shielding in place in the event of, for example, a failure of means attaching the shielding to the inner housing. The shielding is preferably restrained by inwardly protruding bosses of the outer housing. The number of fasteners for the cabinet is substantially reduced over the prior construction because separate infill and cladding panels are not required, and the weight of the cabinet is also substantially reduced.

The inner housing comprises a load bearing enclosure capable of supporting components at any location; such a cabinet is accordingly adaptable to many internal configurations of components, and can be re-used in the case of an alternative configuration without adapter plates and the like.

An x-ray inspection device comprises an x-ray source from which an x-ray beam is emitted, and an image intensifier which receives the beam and causes an image to be formed. An object placed between the source and the intensifier may absorb x-rays, and cause a shadow to appear as the image. By moving the object and intensifier relative to the source, the image may be magnified. A video camera provides real time display of the image on a monitor external to the inspection device.

The object may be placed on a manipulator movable in the X, Y and Z axes, and the intensifier is typically placed on the Z axis in line with the x-ray beam. Such an arrangement permits the object to be moved along the Z axis towards and away from the source, and traversed in the X Y plane. Devices for moving a manipulator in the desired three axes are known.

It would be useful to be able to inspect an object other than along the Z axis, and the present invention provides a compact and relatively simple solution to this requirement.

According to a second aspect of the invention, a movable support of an x-ray inspection device comprises a planar frame, a primary carriage mounted on the frame and movable in the plane of the frame from side to side in a first direction, and drive means to move the carriage with respect to the frame, wherein the carriage is pivotable in said plane about an axis perpendicular to said first direction.

Such an arrangement permits an image intensifier to be mounted on the carriage and be tilted towards a relatively fixed x-ray source as the carriage moves sideways in the frame away from nominal position.

Thus, in the nominal position an x-ray source and an image intensifier are aligned on the Z axis with an object therebetween. By moving the intensifier sideways, and tilting it towards the source, the object may be viewed at an angle, so permitting non-perpendicular inspection at e.g. up to 45°. The object may also be moved sideways in order that the image of a particular feature is in the centre of the field of view, and the object may be moved towards or away from the intensifier in order to change magnification.

Preferably the carriage is pivotable on both sides of the nominal position so as to permit inspection at ±45°, In a preferred embodiment the primary carriage is itself mounted on a secondary carriage which permits tilting in a plane at right angles to the tilting plane of the primary carriage. This arrangement permits all round viewing of an object In an alternative embodiment, the carriage is movable linearly, and is tiltable so as to permit inspection at 0–45°, and a rotary table is provided on the manipulator to support an object. This arrangement also permits all round viewing of an object by rotating the table by up to 360° so that the object is in the line of sight of the image intensifier.

The carriages and manipulator are preferably servo controlled to ensure precise alignment. The rotary table, where provided, is also preferably servo controlled in order to ensure a precise angular displacement from the datum position.

In the preferred embodiment the or each carriage is mounted on upper and lower linear bearings extending across the frame, and is driven in a manner which ensures higher relative velocity in one bearing than the other, preferably by toothed belt drive. This arrangement ensures precise pivoting with respect to the nominal (vertical) position, and ensures that the intensifier axis remains centred.

A single motor may provide toothed belt drive to both the upper and lower bearings, the differential velocity being achieved by drive pinions of different diameter. Such an arrangement is elegant and space efficient.

Each carriage is mounted to the linear bearings with one fixed and one sliding connection in order to permit the connections to move apart during tilting movement of the carriage.

The x-ray inspection device according to the invention may be controlled by conventional joystick technology, or separate controls for individual servo motors.

One difficulty with a typical x-ray imaging device is to be able to set or determine the reference distance from x-ray source and the image intensifier to a support for an object to be imaged. The reference distance requires setting in order to compensate, for example, for manufacturing tolerances or ambient temperature effects, and is preferably adapted for periodic re-setting.

According to a third aspect, a method of determining a reference distance from an image intensifier to a support for an object to be imaged comprises the steps of imaging a plurality of pre-defined locations on said support by means of an x-ray beam perpendicular to the plane of the support, shifting the image intensifier in a plane parallel to the plane of the support, re-imaging said pre-defined locations by means of an x-ray beam non-perpendicular to the plane of the support, determining the angle of said beam with respect to said locations, and calculating said reference distance by means of trigonometry.

Such a method gives a highly accurate means of setting the reference distance. The pre-defined locations are preferably discontinuities in the support which can be detected by software imaging techniques. Preferably such locations are defined by a series of recesses, typically through holes in the support.

In a preferred embodiment said through holes are countersunk to the same extent on both sides so that the respective countersinks meet in the middle. Such a through hole can be recognised relatively easily by imaging software since it remains as a symmetric pattern when viewed at an angle. The countersink angle should not be less than the maximum angle of view. In the preferred embodiment the countersink has an included angle of 90°, and the maximum angle of impinging x-rays is 45°.

In a preferred embodiment the support comprises a rectangular 1 mm plate having through holes of approximately 0.5 mm adjacent the comers thereof, and countersunk on both sides at 45°. Perpendicular imaging of such holes also permits the linear traverse of the image intensifier to be related to the distance between such holes, and accordingly to provide compensation for displacement errors in the case that the support is movable in the X–Y plane. Displacement may be controlled by way of lead screw, belt or any other convenient method. Such a movable support is of course useful in order to centre an area of interest within the field of view of the image intensifier. For example, the number of lead screw rotations can be precisely related to the distance between the discontinuities, and thus highly accurate intermediate positioning of the support is obtained.

One further difficulty with a tilting intensifier is that of setting the distance from the intensifier to area of interest on the object. Typically an object has depth, and the area of interest may not lie in the plane of the support. In the case of axial imaging, in which the x-ray beam is perpendicular to the support plate, no difficulty arises; the area of interest can be magnified at will, and remains in the centre of the field of view.

However, in the case of imaging at an angle, the plane of the area of interest becomes important. If the reference datum is the plane of the support but the area of interest lies outside that plane, magnification at an angle will cause the area of interest to move sideways from the centre of the field of view. This is a serious difficulty at high magnification, and may result in disorientation of the operator. In accordance with a fourth aspect, the invention provides for setting the reference distance from the image intensifier to the object plane of interest.

In a preferred embodiment the method of setting the reference distance comprises the steps of imaging the object by means of an x-ray beam perpendicular to the support plane of the object, causing the area of interest to be centred in the field of view, imaging the object at a first angle, re-centring the area of interest in the field of view, imaging the object at a second greater angle, re-centring the area of interest in the field of view, and repeating the steps of imaging at a successively greater angle, and re-centring until the image remains at the centre of the field of view for all angles of the x-ray beam. By use of simple trigonometrical techniques, this iterative procedure can automatically determine a new reference height and thus ensure that during magnification, the area of interest remains in the centre of the field of view. Re-imaging at increasing angular steps minimises the risk that the area of interest will leave the field of view entirely.

In the case of inspection of an object having repeated features, and mounted on a support movable in the X–Y plane, the setting of the reference distance to the area of interest permits rapid traversing of the object to each repeated feature, without the need for enlarging the image, centring the new feature in the field of view, and magnifying the new area of interest on the repeated feature. Repeatability and speed is consequently enhanced whilst maintaining the same reference distance.

According to a fifth aspect of the invention, a method of controlling such a device comprise the steps of viewing a first x-ray image of an object in the device, manipulating said first image virtually to best show an area of interest, and causing said device to move said object with respect to an x-ray source and/or an x-ray image intensifier in a real time to generate a second image corresponding to said area of interest.

The user can thus see a virtual image of the entire object, manipulate that image using software to select an area or view of interest, and cause other software to move the object to most closely correspond to the virtual image by using the X, Y and Z co-ordinates of the virtual image. A portion of the object may thus be viewed at high magnification whilst the virtual image is retained so as to permit the user to have an overview of the direction of view with respect to the entire object.

The virtual and real time image are preferably displayed on the same monitor at the same time, the virtual image being located for example in the upper right hand corner of the monitor screen. The virtual image may be created or recreated by real time imaging of an object. In a preferred embodiment, the virtual image is a frozen real time image created solely for the purpose of manipulation and in order to allow the user to quickly select an area of interest rather than manipulate the object in real time until the desired region is in view. The object may be automatically manipulated in real time in order to generate sufficient data to create the virtual reference image. This may be particularly useful where the object is larger than the image intensifier, so that the image intensifier scans the object to determine the boundary thereof, and subsequently constructs a virtual image of the object for the purposes of manipulation.

In use the real time image may be dragged across the screen, or otherwise manipulated by computer mouse, the apparent manipulation causing the object to be moved in real time so that the real time image moves to the desired screen location. Such object movement is preferably quite fast so that the user does not notice a significant lag between mouse operation and the real time movement of the object which results in movement of the real time image.

Typically the virtual image will be created by software imaging techniques at the start of an inspection routine. Once created, the initial image remains as a navigation aid, and the field of view of the object in real time is represented on the virtual image by e.g. a box surrounding the corresponding portion. The size of this box preferably increases or decreases with magnification of the object, and thus can correspond substantially to the instant field of view. The virtual image may tilt or otherwise change attitude to correspond to the direction of viewing of the object.

In the case where the support for the object is rotatable, the attitude of the real time image of the object with respect to the virtual image will change. Preferably the rotatable support has a reference position at the start of an inspection routine, and an arrow indicates the instant direction of view on the virtual image, for example by pointing at a box defining the field of view. Alternatively the virtual image may rotate in synchronisation with the rotatable table.

Other features of the invention will be apparent from the following description of a preferred embodiment shown by way of example only in the accompanying drawings in which.

Figure 1:
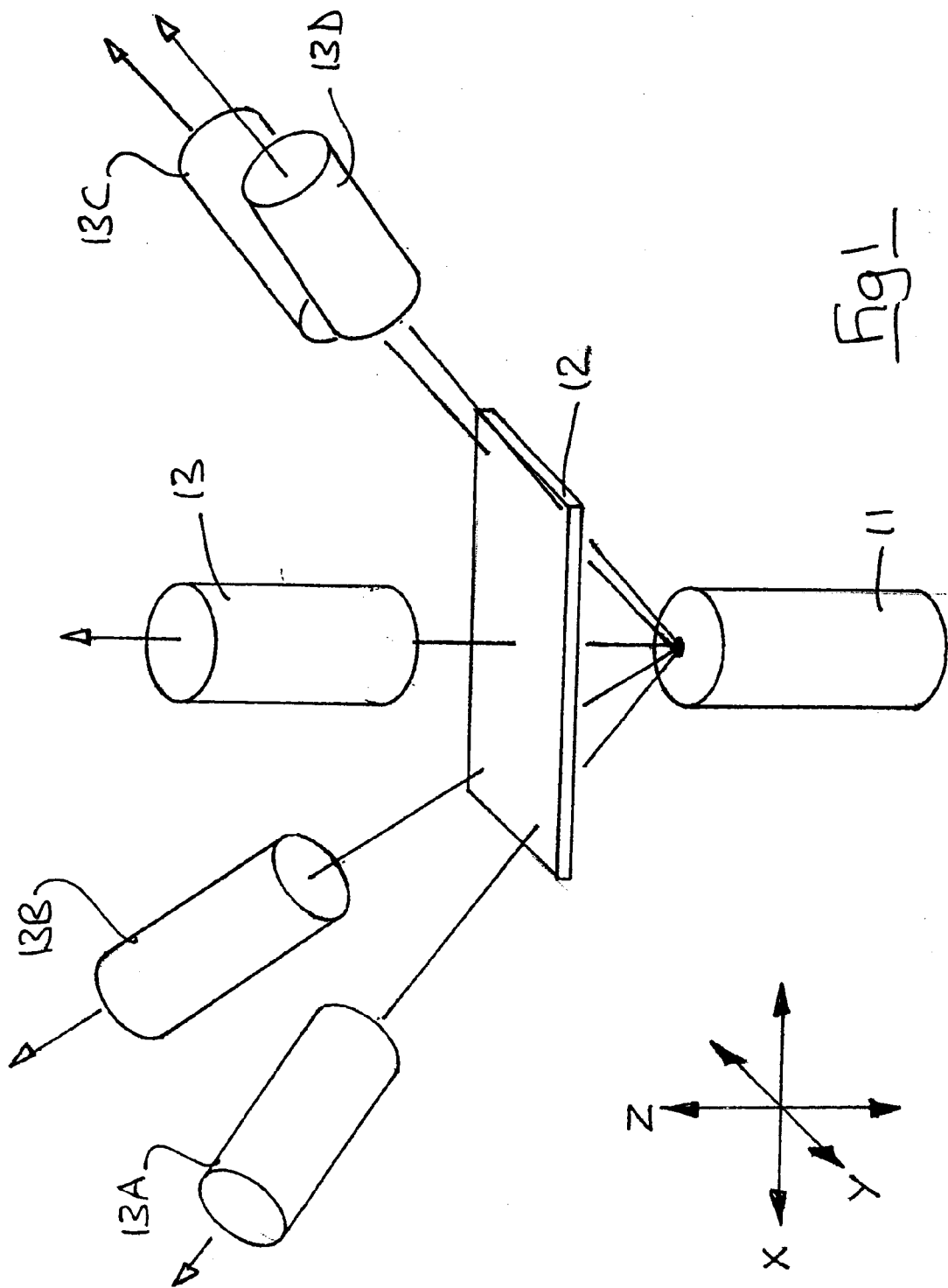
FIG. 1 is a schematic illustration of an x-ray tube, object support surface and arcuately movable image intensifier.

FIG. 1 illustrates schematically an x-ray tube 11 from which x-rays pass through a manipulator plate 12 to an image intensifier 13. The x-ray tube 11 is fixed whereas the image intensifier 13 is movable between predetermined extremes of movement 13A–13D so as to remain aligned with the x-ray source. At the extremes, the image intensifier is aligned with x-rays passing from the source close to the corners of the plate 12, as illustrated. The mechanism for moving the image intensifier is described subsequently, and is operable to place the intensifier in any position between the four extremes illustrated and aligned with the focal point 14 of the x-ray source.

The manipulator plate is also movable on the X, Y, & Z axes in order to position an object in the centre of the field of view of the image intensifier, and in order to change the field of view by moving the plate 12 towards and away from the intensifier 13. The means for moving the plate can be any suitable and conventional 3 axis motor drive.

It will be understood that a rotatable support may be provided on the plate 12, which in conjunction with an image intensifier tiltable in a single plane, can provide an all round view of an object. X–Y movement of the plate 12 remains desirable in this alternative in order to centre the field of view.

Figure 2:
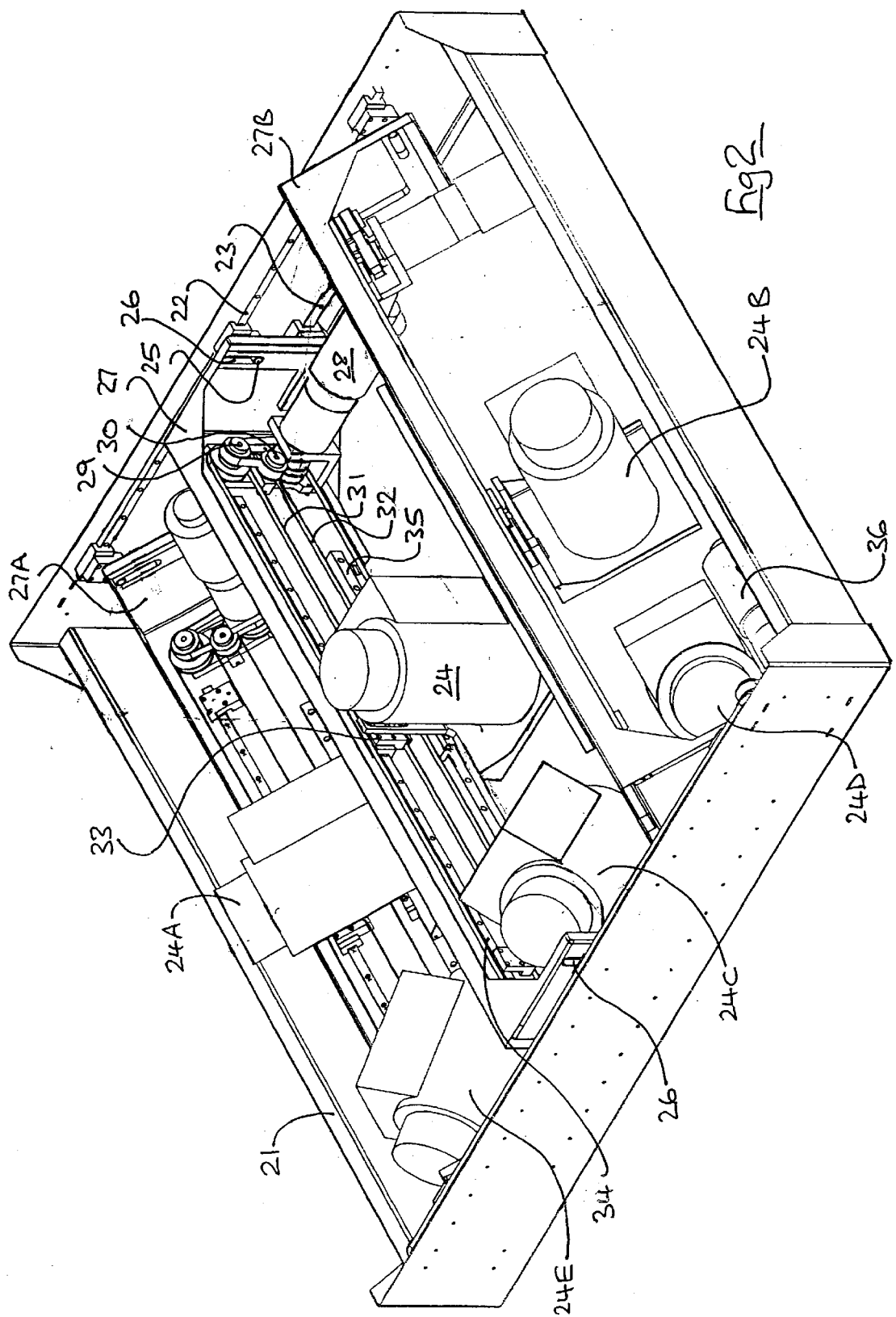
FIG. 2 is a perspective view of a device for moving an image intensifier arcuately in mutually perpendicular directions.

The device for moving the image intensifier is illustrated in FIG. 2. A generally rectangular frame 21 includes on opposite sides pairs of upper and lower linear bearings 22,23. These support between them a carriage 27 which extends the full width of the frame and can slide from one end of the frame to the other.

The connection between the carriage and the lower bearing 23 is a simple pivot, but the connection to the upper bearing is by means of a pivot pin 25 running in a slot 26 of the carriage. This arrangement permits the carriage to rock from side to side through an arc determined by the length of the slot 26, but typically ±45°.

The carriage 27 is driven from one end of the frame to the other by an electric motor which also controls the attitude of the carriage by means yet to be described. An image intensifier 24 is mounted on the carriage.

In FIG. 2 the carriage 27 is shown in the mid-position, and in both tilted end positions 27A, 27B; the image intensifier 24A, 24B being tilted accordingly.

The mounting of the image intensifier 24 to the carriage 27 is by means of two further upper and lower linear bearings 34, 35. The arrangement is similar to that of the bearings 22, 23 with the lower bearing being a simple pivot whereas the upper bearing is by way of a pin and slot. This arrangement permits rocking of the intensifier in a plane at right angles to the rocking plane of the carriage 27, and FIG. 2 illustrates the mid-position 24C at one side.

It will be apparent that combined rocking in both planes causes the intensifier to adopt a compound tilt at the corners of the frame, marked 24D, 24E.

The attitude of the intensifier 24 with respect to the carriage 27 is determined by an electric motor 28 mounted on the carriage at one end and having a belt drive to upper and lower drive wheels 29, 30 also mounted on the carriage. Corresponding upper and lower idler wheels are provided at the other end of the carriage.

Continuous drive belts 31, 32 run between the upper and lower drive and idler wheel pairs and are attached to a corresponding trunnion mounted on the adjacent linear bearing 34, 35, and which is connected by a respective coupling to the intensifier 24. The upper trunnion 33 only can be seen. The drive belts and wheels are toothed so as to transmit movement precisely from the motor 28 to the trunnions.

The upper and lower drive wheels 29, 30 have a different diameter such that the upper belt 31 has a greater travel than the lower belt 32 for a given angular rotation of the motor 28. In this way the intensifier 24 is tilted from side to side as it is driven by the motor 28 from end to end of the carriage.

By suitable choice of wheel diameter, the image intensifier 24 can be made to follow a path centred on the focal point of the x-ray source.

The arrangement for driving and tilting the carriage 27 with respect to the frame 21 is identical, the motor 36 being illustrated, but the drive belts and wheels being hidden from view.

By simultaneous operation of motors 28, 36, the intensifier will follow an arcuate path within the limits of the frame 21 and always centred on the focal point of the x-ray source, as shown schematically in FIG. 1.

Figure 3:
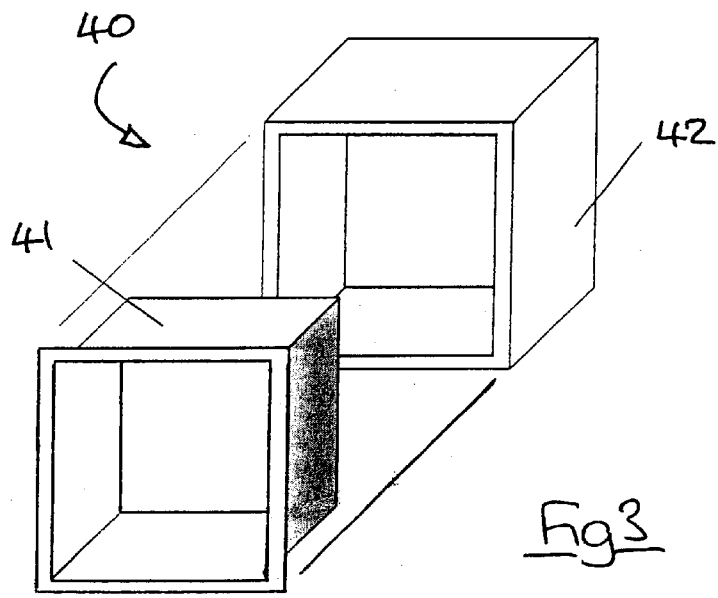
FIG. 3 illustrates the construction of a cabinet according to the invention.

FIG. 3 illustrates in general terms the arrangement of a cabinet 40 into which the x-ray source, manipulator table and image intensifier assembly are positioned. The cabinet comprises an inner enclosure 41 of e.g. steel, comprising an open mouthed box adapted to house the components illustrated in FIGS. 1 and 2, and an outer enclosure 42 comprising a second box and which has a cosmetically attractive appearance. The inner and outer boxes 41, 42 have conventional means to join them together at a spacing, and together they form a stiff and strong structure adapted to maintain the internal parts in a rigid and defined configuration.

Prior to assembly, the inner box is shielded with lead sheet, and this conveniently lies in the space between the inner and outer boxes, which space contributes to the rigidity of the cabinet.

Shielding can relatively easily be applied over the entire surface of the inner enclosure 41, and may be attached by adhesive, and supported by bosses pressed in the walls of the inner enclosure. The outer enclosure may also have internal bosses to fit closely against the lead shielding so as to maintain integrity of the shielding in the event that a glued fastening should fail.

The enclosure of the lead shielding has the advantage that it cannot be tampered with, or distributed as might be the case with removable cladding panels. Furthermore the shielding can be applied without regard to cosmetic appearance since in use it is permanently enclosed by the outer enclosure 42; this means that function of shielding the radiation hazard is not compromised by aesthetic considerations.

A double skin lead shielded door is attached to the cabinet by any suitable method in order to fully enclose the x-ray apparatus in use.

In a third aspect, the invention includes a method of controlling the x-ray device by means of computer and video display.

As has been mentioned the image on the intensifier 24 is relayed by video camera to a monitor external to the cabinet. Control apparatus is provided whereby the image intensifier and manipulator table can be moved in order to change the magnification/field of view of an object on the table, and to change the angle of view through the object.

At high magnification, the operator may become disorientated and unable to decide in which direction to move the object in real time in order to view the next feature of interest.

The invention provides a virtually created image in order to assist the operator.

Figure 4:
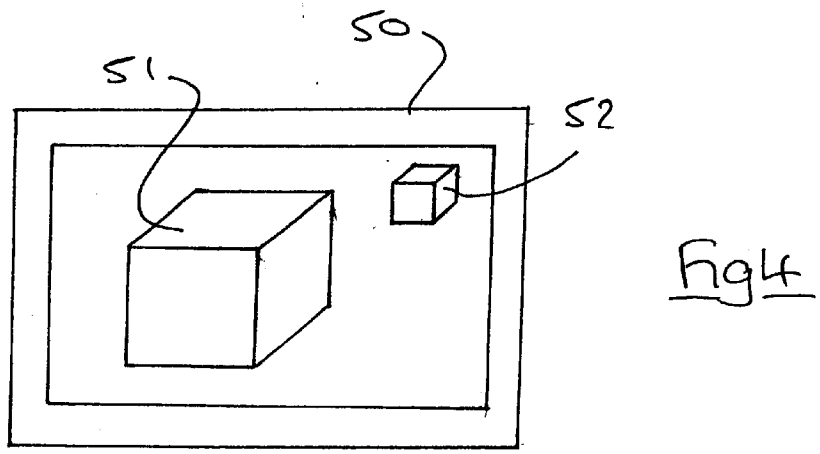
FIG. 4 illustrates a video image according to the invention.

FIG. 4 illustrates a video monitor 50 having a real time image 51 and a virtual image 52 in the top right hand corner.

The virtual image 52 is obtained by scanning an object on the manipulator to determine its boundary, and electronically constructing a two dimensional representation using known imaging software techniques. The virtual image does not need to show all of the detail of the object, but the boundaries should be reasonably defined for reasons appearing below.

The real time image 51 is relayed by video camera from the image intensifier within the cabinet.

Figure 5:
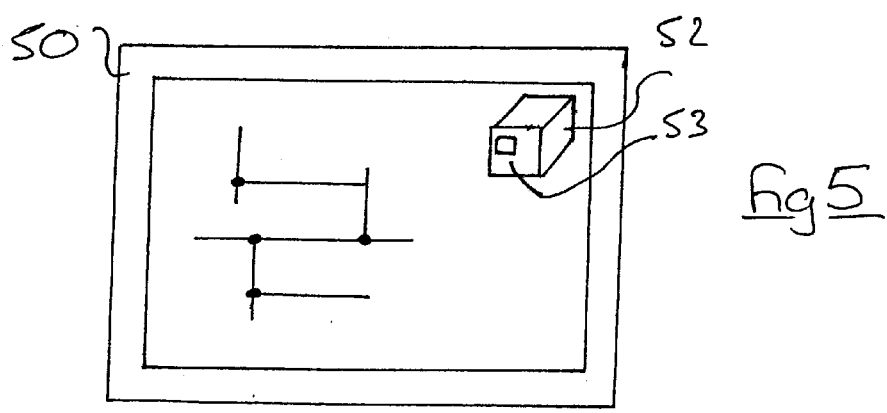
FIG. 5 illustrates a magnified image corresponding to FIG. 4.

FIG. 5 illustrates schematically the view on the video monitor which may appear should the operator zoom onto the object and increase the magnification thereof. In these circumstances the operator may become disoriented but the virtual image shows by means of box 53, the corresponding area of view. By this means the operator is able to ensure that the desired area of the object is being inspected. The size of the box 53 may change according to the field of view of the real time image, so that the perimeter of the box 53 agrees precisely with the boundary of the real time image at all times.

In cases where the real time image is taken at an angle through the object, the virtual image may rotate in order to present to the operator an appropriate view.

As an alternative, the area of interest may be indicated on the virtual image by means of an arrow.

In the case of a rotatable object support, the direction of view may be indicated on the virtual image by means of e.g. an arrow.

Control software may also be included to permit dragging of the real time image so as to view an adjacent area, or to centre a feature on the monitor. Dragging of the image by using a computer mouse causes servo motors of the manipulator table to move the object in the desired direction, so that the real time image quickly follows and replaces the previous real time image. Image replacement may be stepwise and rapid, and be in conjunction with a corresponding change in the box 53 on the virtual image 52 Zoom of the object may be accomplished by means of a finger wheel of a computer mouse.

The means of identifying the area of view on the virtual image may be of any other suitable kind, for example colour highlight or circle, and the virtual image may be displayed in any suitable area of the monitor.

In order to set certain reference dimensions between the image intensifier and the support for the object, the device may include imaging software capable of recognising features provided on the support. The feature may be a recess or hole, and certain dimensions may be determined by using trigonometrical techniques from the measurement of other dimensions and of angles.

Known imaging techniques are capable of recognising a round hole when viewed from above. Such a hole must also be recognised at an angle if trigonometrical techniques are to be useful, but a round hole in a plate does not present a symmetrical image when tilted and imaged by x-ray.

Figure 6:
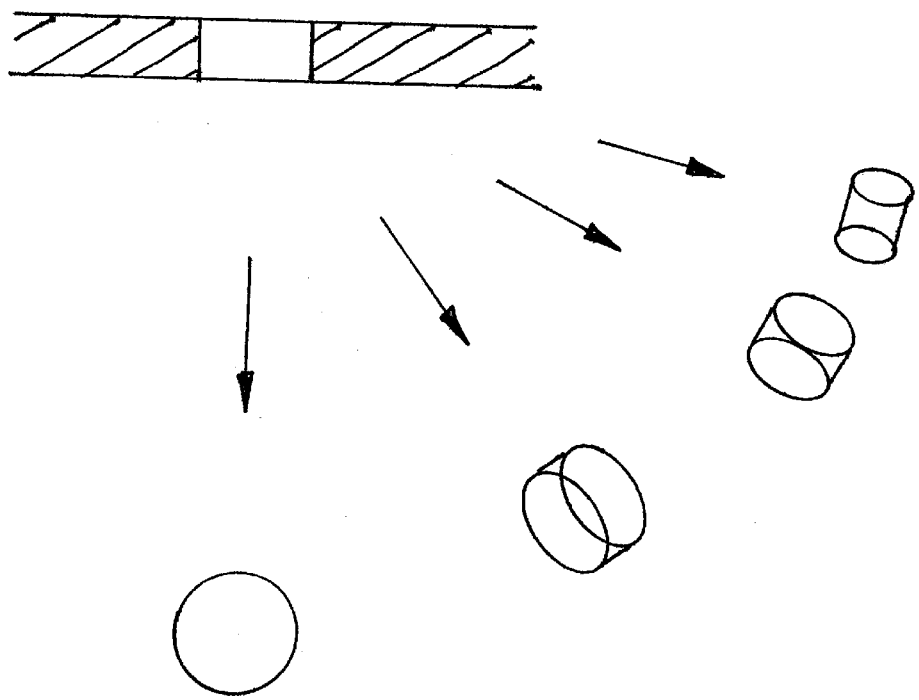
FIG. 6 illustrates software imaging of a plain through hole.

FIG. 6 shows a range of x-ray images of a plain through hole. The image would be substantially identical for a blind hole. It will be noted that the overall shape of the image changes substantially as the angle of the x-ray beam increases (represented by the arrows), from a circle to overlapping ellipses, to spaced ellipses. Such a range of images is rather difficult to recognise with conventional monochrome image recognition software because certain areas are light, certain areas are dark and certain areas are somewhat grey. For example the most oblique image in FIG. 6 has two light ellipses, a grey linking region, and a surrounding dark region. There is a consequent risk in setting the light/dark threshold, that grey areas will not be consistently treated as either light or dark, and the centre of the image may be difficult to locate.

Figure 7:
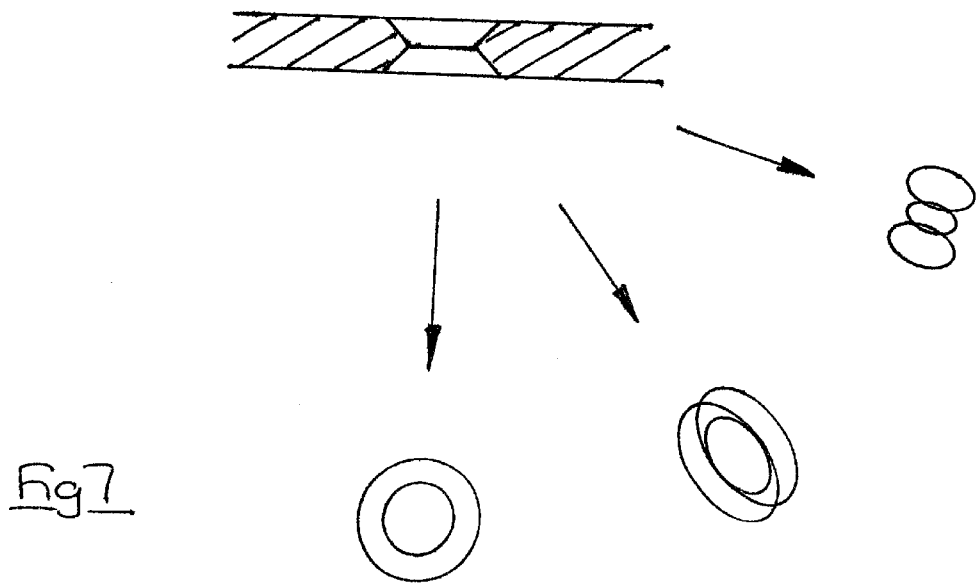
FIG. 7 illustrates software imaging of a countersunk through hole.

FIG. 7 shows a range of images of a through hole countersunk from both sides to an equal extent. As will be quickly noted, this arrangement gives an image with a centre circle or ellipse at all angles, and is thus much easier for image recognition software to recognise. Most importantly the image has a single light centre, and can be detected by image recognition software having a simple light/dark threshold. In this case there is little danger in setting the threshold low so that grey and light areas are detected equally by monochrome image recognition software, because the grey areas are symmetrically disposed around the single light central region. Such an aperture is thus preferred for use in x-ray inspection devices of the kind described herein which utilise imaging software techniques to perform initialisation procedures.

What is claimed is:

1. A method of controlling an x-ray inspection device comprising the steps of:
    viewing a first virtual x-ray image of an object in the device;
    manipulating said first image to best show an area of interest; and
    causing said device to move said object with respect to an x-ray source and/or an x-ray image intensifier in a real time to generate a second image corresponding to said area of interest, said first and second images being displayed simultaneously.

2. A method as claimed in claim 1 wherein the virtual and real time image are displayed on the same monitor at the same time.

3. A method as claimed in claim 1 wherein the virtual image is created or recreated by real time imaging of an object.

4. A method of controlling an x-ray inspection device comprising the steps of:
    viewing a first x-ray image of an object in the device;
    manipulating said first image virtually to best show an area of interest;
    causing said device to move said object with respect to an x-ray source and/or an x-ray image intensifier in a real time to generate a second image corresponding to said area of interest; and
    determining a reference distance from an image intensifier to a support for an object to be imaged, comprising the steps of:
        imaging a plurality of pre-defined locations on said support by means of an x-ray beam perpendicular to the plane of the support;
        shifting the image intensifier in a plane parallel to the plane of the support;
        re-imaging said pre-defined locations by means of an x-ray beam non-perpendicular to the plane of the support;
        determining the angle of said beam with respect to said locations; and
        calculating said reference distance by means of trigonometry.

5. A method of controlling an x-ray inspection device comprising the steps of:
    viewing a first x-ray image of an object in the device;
    manipulating said first image virtually to best show an area of interest;
    causing said device to move said object with respect to an x-ray source and/or an x-ray image intensifier in a real time to generate a second image corresponding to said area of interest; and
    setting a reference distance from an image intensifier to an object plane of interest, comprising the steps of:
        causing an area of interest to be centered in the field of view;
        imaging the object at a first angle;
        re-centering the area of interest in the field of view;
        imaging the object at a second greater angle;
        re-centering the area of interest in the field of view, and repeating the steps of imaging at a successively greater angle; and
        re-centering until the image remains at the center of the field of view of all angles of the x-ray beam.

* * * * *